(12) United States Patent  
Moschell et al.

(10) Patent No.: US 10,527,636 B2  
(45) Date of Patent: Jan. 7, 2020

(54) INSTRUMENT INTERFACE WITH PRESENTATION UNIT DISPLAY

(71) Applicant: Beckman Coulter, Inc., Brea, CA (US)

(72) Inventors: Rachel E. Moschell, Zionsville, IN (US); Jessica A. Zeckel, Carmel, IN (US); Robert J. Zigon, Carmel, IN (US)

(73) Assignee: Beckman Coulter, Inc., Brea, CA (US)

( * ) Notice: Subject to any disclaimer, the term of this patent is extended or adjusted under 35 U.S.C. 154(b) by 149 days.

(21) Appl. No.: 15/127,656

(22) PCT Filed: Mar. 18, 2015

(86) PCT No.: PCT/US2015/021332  
§ 371 (c)(1),  
(2) Date: Sep. 20, 2016

(87) PCT Pub. No.: WO2015/143084  
PCT Pub. Date: Sep. 24, 2015

(65) Prior Publication Data  
US 2017/0176480 A1    Jun. 22, 2017

Related U.S. Application Data

(60) Provisional application No. 61/955,956, filed on Mar. 20, 2014.

(51) Int. Cl.  
*G01N 15/14*         (2006.01)  
*G01N 35/00*         (2006.01)  
*G01N 35/04*         (2006.01)  
*G06F 3/0481*        (2013.01)  
*G06F 3/0484*        (2013.01)  
(Continued)

(52) U.S. Cl.  
CPC ....... *G01N 35/00722* (2013.01); *G01N 15/14* (2013.01); *G01N 35/00584* (2013.01); *G01N 2035/0091* (2013.01); *G01N 2035/00891* (2013.01); *G01N 2035/0441* (2013.01); *G06F 3/0486* (2013.01); *G06F 3/04817* (2013.01); *G06F 3/04842* (2013.01); *G06F 3/04847* (2013.01); *G06F 3/04883* (2013.01)

(58) Field of Classification Search  
CPC ............................................... G01N 35/00722  
See application file for complete search history.

(56) References Cited

U.S. PATENT DOCUMENTS

2006/0004526 A1    1/2006  Hadd et al.  
2008/0014571 A1    1/2008  Teich et al.  
2008/0263468 A1   10/2008  Cappione et al.  
(Continued)

OTHER PUBLICATIONS

International Search Report for PCT/US2015/021332, dated Jun. 9, 2015.

*Primary Examiner* — Clayton E. LaBalle  
*Assistant Examiner* — Dennis Hancock  
(74) *Attorney, Agent, or Firm* — Merchant & Gould P.C.

(57) ABSTRACT

A user interface for an instrument that processes samples from sample containers supported on a presentation unit. The user interface includes a presentation unit display that includes a graphical representation of the presentation unit. The presentation unit display receives inputs therein to define instructions for the processing of the samples by the instrument. The presentation unit display also displays a status while the samples are being processed.

26 Claims, 12 Drawing Sheets

(51) Int. Cl.
G06F 3/0486 (2013.01)
G06F 3/0488 (2013.01)

(56) References Cited

U.S. PATENT DOCUMENTS

2013/0009988 A1    1/2013  Tokunaga et al.
2014/0314300 A1*  10/2014  Kaufman ........... G06K 9/00127
                                                              382/133

* cited by examiner

INSTRUMENT INTERFACE WITH PRESENTATION UNIT DISPLAY

CROSS-REFERENCE TO RELATED APPLICATION(S)

This application is a U.S. National Stage application of PCT/US2015/021332, filed Mar. 18, 2015, which claims benefit of U.S. Provisional Patent Application Ser. No. 61/955,956, filed Mar. 20, 2014, and which applications are hereby incorporated by reference in their entireties. To the extent appropriate, a claim of priority is made to each of the above disclosed applications.

BACKGROUND

A flow cytometer is one example of an instrument that performs an analysis of a sample. In some cases, the instrument is capable of receiving multiple samples. Each of the samples is contained in a sample container, such as a test tube. The sample containers are placed into a support structure commonly referred to as a carousel. The carousel holds the sample containers in an orderly fashion so that the samples contained therein can be selectively processed and analyzed by the instrument.

In order for the instrument to properly analyze each sample, an operator provides instructions to the instrument that define how the samples should be processed. In some instruments, a user interface is provided that includes a table structure having rows and columns through which the instructions are provided to the instrument. Because the sample containers are not themselves arranged in a corresponding table structure, errors can occur when the operator is entering the instructions into the table structure.

SUMMARY

In general terms, this disclosure is directed to a user interface for an instrument. In one possible configuration and by non-limiting example, the user interface includes a presentation unit display for providing instructions to the instrument. The presentation unit display has a similar appearance to the presentation unit of the instrument allowing the user to easily compare the presentation unit display with the presentation unit containing the samples. Various aspects are described in this disclosure, which include, but are not limited to, the following aspects.

One aspect is an instrument system comprising: an instrument configured to analyze samples; a carousel configured to support a plurality of sample containers containing the samples to be analyzed by the instrument; and a computing device including a display, the computing device configured to generate a user interface including a carousel display, the carousel display including a graphical representation of the carousel, wherein the carousel display is configured to receive inputs from an operator to define instructions for analysis of the samples by the instrument.

Another aspect is a computing device comprising: a display device; at least one processing device; and at least one computer readable storage device, the computer readable storage device storing data instructions, which when executed by the at least one processing device cause the at least one processing device to: generate a user interface on the display device, the user interface including a graphical representation of a carousel of an instrument; and receive inputs, at least one of the inputs being provided into the graphical representation of the carousel, the inputs defining instructions for analysis of a sample by the instrument.

A further aspect is a method of operating an instrument, the method comprising: processing one or more samples with the instrument, the one or more samples being contained in sample containers supported in a carousel; and generating a user interface with a computing device during the processing of the one or more samples, the user interface including a carousel display including a graphical representation of the carousel, the carousel display showing a current status of the processing of the one or more samples.

Another aspect is an instrument system comprising: an instrument configured to analyze samples; a presentation unit configured to support a plurality of sample containers containing the samples to be analyzed by the instrument; and a computing device including a display, the computing device configured to generate a user interface including a presentation unit display, the presentation unit display including a graphical representation of the presentation unit, wherein the presentation unit display is configured to receive inputs from an operator to define instructions for analysis of the samples by the instrument.

A further aspect is a computing device comprising: a display device; at least one processing device; and at least one computer readable storage device, the computer readable storage device storing data instructions, which when executed by the at least one processing device cause the at least one processing device to: generate a user interface on the display device, the user interface including a graphical representation of a presentation unit of an instrument; and receive inputs, at least one of the inputs being provided into the graphical representation of the presentation unit, the inputs defining instructions for analysis of a sample by the instrument.

Yet another aspect is a method of operating an instrument, the method comprising: processing one or more samples with the instrument, the one or more samples being contained in sample containers supported in a presentation unit; and generating a user interface with a computing device during the processing of the one or more samples, the user interface including a presentation unit display including a graphical representation of the presentation unit, the presentation unit display showing a current status of the processing of the one or more samples.

DETAILED DESCRIPTION

Figure 1:
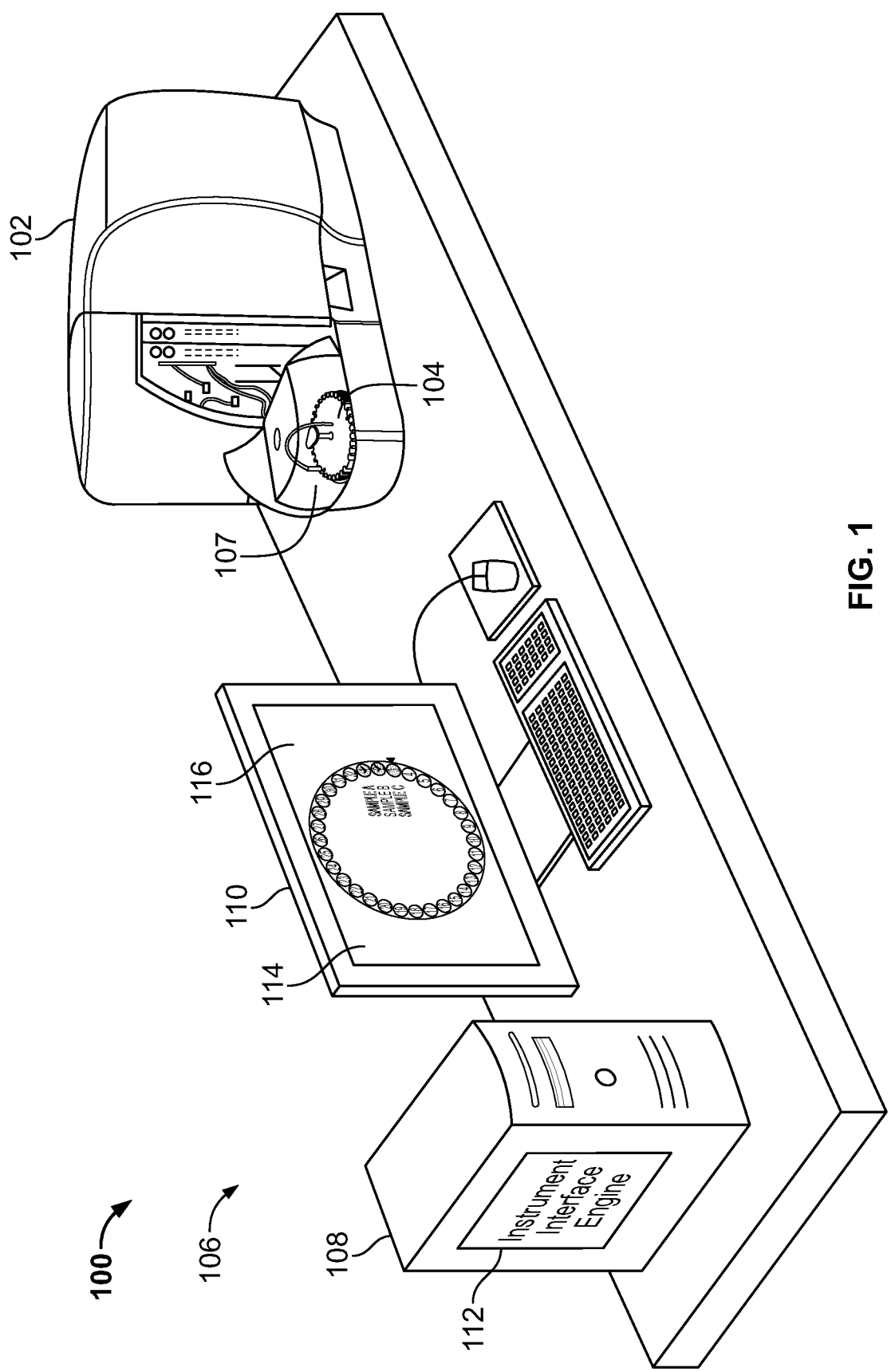
FIG. 1 is a schematic diagram illustrating an example of an instrument system.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

The present disclosure relates to a user interface having a presentation unit display. In some embodiments the presentation unit display includes a graphical representation of a presentation unit. A presentation unit is, for example, a support structure configured to present samples to an instrument. One example of a presentation unit is a carousel. A carousel often has a rounded configuration and includes container positions formed therein that are sized and positioned to receive sample containers therein. A turntable is used to rotate the carousel and the sample containers so that the samples can be introduced into and evaluated by the instrument. Other examples of presentation units include sample racks, plates, and trays. Racks, plates, and trays also include a support structure, such as having a square or rectangular shape, or other possible shapes. Racks, plates, and trays can include container positions formed therein, such as arranged in a circular arrangement, a row, a grid (such as having a plurality of rows and columns), a serpentine arrangement, or in other possible arrangements. The following disclosure refers primarily to example embodiments in which the presentation unit is a carousel. The same or similar principles, features, structures, systems, and methods can also be used in other embodiments utilizing other presentation units, such as sample racks, plates, and trays, and corresponding presentation unit displays, according to the present disclosure.

FIG. 1 is schematic diagram illustrating an example instrument system 100. In this example, the instrument system includes an instrument 102, a carousel 104, and a computing device 106. In some embodiments the instrument 102 includes a sample loading region 107. In some embodiments the computing device 106 includes a computer 108 and a display device 110. In some embodiments the computer 108 includes an instrument interface engine 112, which generates a user interface 114 on the display device 110. Further, in some embodiments the user interface 114 includes a carousel display 116.

Figure 2:
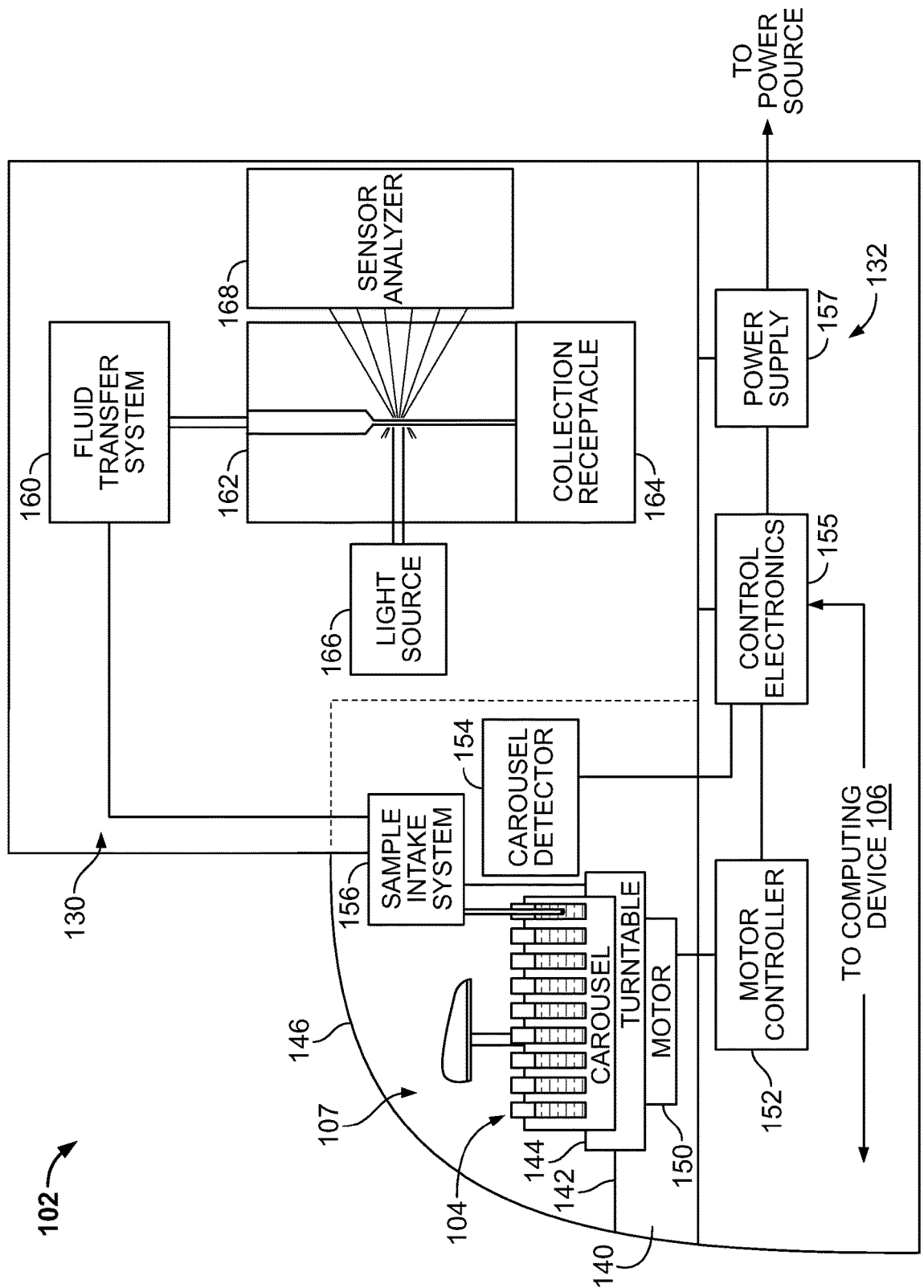
FIG. 2 is a schematic block diagram of an example instrument.

The instrument 102 is a device that performs an analysis on a sample. In one example, the instrument 102 is a flow cytometer. Other embodiments include other types of instruments, such as a chemistry analyzer and a hematology machine. The instrument 102 typically includes a sample loading region 107 that includes or is configured to receive the carousel 104. One or more samples are arranged within sample containers, such as test tubes, on the carousel 104, and the instrument 102 extracts the samples from the sample containers to analyze the samples. As used herein, samples are the contents of sample containers provided to the carousel 104. Examples of samples include blood, urine, sea water, fresh water, and prepared/processed samples including lysed, fixed, and centrifuged samples. Some samples contain sample particles. Examples of sample particles include beads, bacteria, yeast, plankton, microparticles (e.g., from a plasma membrane of a cell), mitochondria, viruses and cells (including white blood cells, peripheral epithelial cells, and circulating tumor cells), and labeled particles and cells (including cells labeled with an antibody conjugated to a fluorescent dye). In some embodiments the samples include particles of interest that are analyzed by the instrument 102, but as used herein, a sample can also be a substance used by the instrument system 100, such as a cleaning fluid, which is not itself intended to be analyzed by the instrument 102. Some embodiments include an automated sample loader that operates to automatically extract the samples from the carousel 104. An example of the instrument 102 is shown in FIG. 2.

Figure 3:
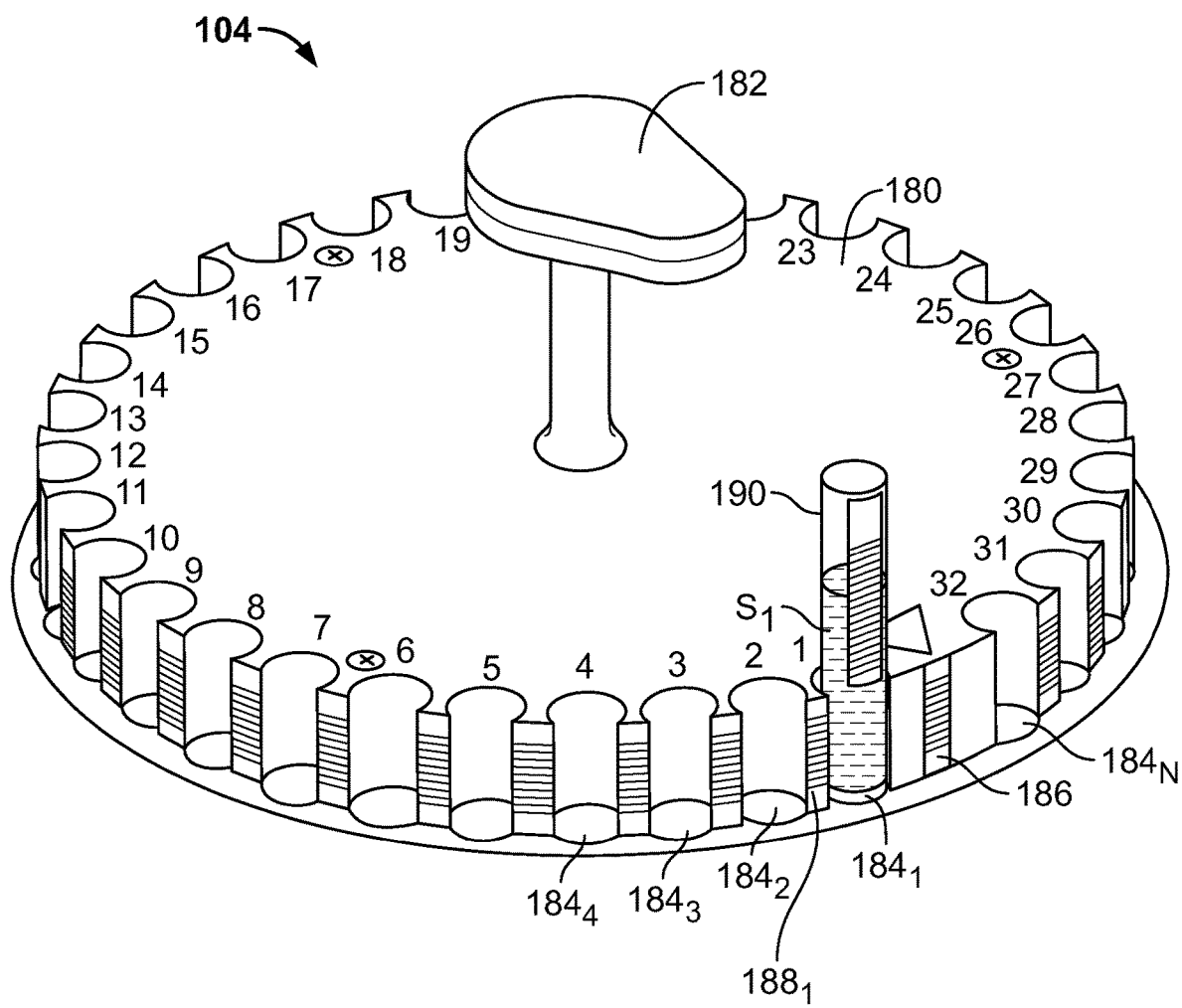
FIG. 3 is a perspective view of an example carousel.

The carousel 104 is configured to support a plurality of sample containers to permit the instrument 102 to process the samples contained therein. In some embodiments the carousel is a removable part of the automated sample loader of the instrument 102. An example of a carousel 104 is shown in FIG. 3.

The computing device 106 includes at least one processing device and at least one computer readable storage device, and operates to control at least some of the operations of the instrument 102. In some embodiments the computing device 106 is in data communication with the instrument 102, such as through one or more electrical cables or wirelessly through wireless communication devices. In other embodiments the computing device 106 is integral to the instrument 102.

In the illustrated example, the computing device 106 includes a computer 108 and a display device 110. The computer can be of a variety of different forms, such as a desktop computer, a laptop computer, a tablet computer, a smartphone, a wearable computing device, or other forms. The display device 110 can be part of the computer 108 or a separate device, such as a computer monitor. The computing device 106 also includes one or more input devices, such as described in further detail herein.

In some embodiments the computing device 106 includes an instrument interface engine 112, which generates a user interface 114 that is displayed by the display device 110. In some embodiments the user interface 114 includes a carousel display 116, which generates a graphical representation of the carousel 104. In some embodiments the operator can interact with the carousel display 116 to configure or control the operation of the instrument 102. The carousel display 116 provides an intuitive interface that mimics the appearance of the physical carousel 104. This can make configuration and control of the instrument 102 easier, for example, and can reduce the chance that errors are made by the operator. The instrument interface engine 112 and the carousel display 116 are illustrated and described in further detail herein with reference to FIGS. 5-11.

FIG. 2 is a schematic block diagram of an example instrument 102. In this example, the instrument 102 is a flow cytometer, and includes the sample loading region 107, a sample analysis region 130, and other electronic circuitry 132.

The instrument 102 operates to process and analyze samples. In some embodiments the samples are introduced into the instrument 102 at a sample loading region 107. In this example, the sample loading region 107 includes a housing 140 defining an interior space, the housing 140 including a base 142, a turntable 144, and a cover 146. In some embodiments the instrument 102 further includes a motor 150 and motor controller 152 operable to rotate the turntable 144, a carousel detector 154, and a sample intake system 156.

To access the sample loading region 107, the cover 146 can be opened by pivoting about a hinged connection between the base 142 and the cover 146. When in the open position, the cover 146 provides access to the interior space. The turntable 144 is provided in the interior space and is shaped and sized to receive the carousel 104. The turntable 144 is coupled to a motor 150, controlled by the motor controller 152, to rotate the carousel 104 as discussed herein. Once the carousel 104 is properly positioned in the sample loading region 107, the cover 146 is returned to the closed position.

Some embodiments include a carousel detector 154. The carousel detector 154 can be used, for example, to read an identification number of the carousel 104 or one or more of the sample containers arranged on the carousel 104. One example of the carousel detector 154 is a barcode scanner. Other embodiments utilize other detectors, such as optical or image capturing devices, radio frequency identification devices, and the like. In the case of a barcode scanner, the carousel detector 154 operates to read one or more barcodes arranged on the carousel 104 or the sample container, such as shown in the example of FIG. 3.

The instrument 102 also includes a sample intake system 156, which operates to extract at least a portion of a sample from a sample container on the carousel 104. In some embodiments the sample intake system 156 includes a mechanical system that retrieves the sample container from the carousel 104, agitates the sample container, and aspirates at least a portion of the sample from the sample container for further analysis by the instrument 102.

In the illustrated example, the instrument 102 further includes a sample analysis region 130, which operates to analyze the sample obtained from the sample loading region 107. In this example of an instrument 102 being a flow cytometer, the sample analysis region 130 includes a fluid transfer system 160, a flow cell 162, a collection receptacle 164, a light source 166, and a sensor analyzer 168.

The sample analysis region 130 processes and analyses the sample from the sample loading region 107, such as to determine one or more characteristics of the sample, such as one or more contents of the sample, particle sizes, particle quantities, and or other characteristics.

In this example, a fluid transfer system 160, such as including fluid conduits, one or more pumps, and valves, operates to transfer the sample from the sample intake system 156 to the flow cell 162.

The flow cell 162 includes a narrow aperture which causes the particles in the sample to be arranged into a narrow stream. The sample passes through the flow cell 162 and then into the collection receptacle 164.

While the sample is passing through the flow cell 162, a light source 166 generates light that illuminates the sample. The light source 166 can include one or multiple light sources, which can be selectively operated independently, simultaneously, or in combinations.

After the light passes through the sample, the sensor analyzer 168 operates to detect and analyze the light. In some embodiments the sensor analyzer 168 includes a plurality of light detectors. By evaluating the scattering and fluorescence of the light after illuminating the sample, the instrument 102 can determine various characteristics of the sample.

In some embodiments the instrument 102 includes other electronic circuitry 132, such as including the motor controller 152, control electronics 155, and a power supply 157. The motor controller 152 typically operates to convert digital control signals from the control electronics 155 into electrical signals needed to power and control the motor 150. The control electronics 155 typically include at least one processing device and at least one computer readable storage device. The control electronics 155 are in data communication with the computing device 106 (shown in FIG. 1), as discussed in further detail herein. The power supply 157 provides power to the electronic circuitry 132, such as from an external power source.

FIG. 3 is a perspective view of an example carousel 104. In this example, the carousel 104 includes a body 180 and a handle 182. The body 180 includes container positions 184 (including container positions $184_1$, $184_2$, . . . $184_N$), carousel identifier 186, and position identifiers 188 (including position identifiers $188_1$, $188_2$, . . . $188_N$). One or more sample containers 190 (including sample containers $190_1$, $190_2$, . . . $190_N$) containing a sample S (including samples $S_1$, $S_2$, . . . $S_N$) can be arranged in the carousel 104.

The carousel 104 is formed of a material such as injection molded plastic, or other suitable material or combinations of materials.

In some embodiments the body 180 has a disc shape, having a flat upper surface, a lower surface, and a sidewall. When viewed from the top, the body 180 has a circular shape. Container positions 184 are arranged about the outer perimeter of the body, having a shape configured to receive and support the sample containers 190 in an upright position therein. As one example, the container positions 184 include a bottom surface and a sidewall forming a cylindrical shaped receptacle. In some embodiments a side of the container position 184 extends through the outer perimeter of the body 180 so that even the lower portion of the sample container 190 (and the sample S contained therein) can be viewed from the side of the carousel 104 when the sample container 190 is arranged in the container position 184.

Some embodiments include identifiers including a carousel identifier 186 and/or position identifiers 188. For example, a carousel identifier 186 is provided at an origin position of the carousel 104, adjacent the first sample container position $184_1$. In this example the carousel identifier 186 is a barcode that encodes a carousel identification code that can be used by the instrument to identify the carousel 104, and to permit the instrument and the operator to distinguish between multiple carousels 104. Position identifiers 188 are included adjacent each container position 184, which encode a position identification code that can be used by the instrument to determine a current position of the carousel 104 as it rotates on the turntable 144 (FIG. 2). For example, the position identifier $188_1$ is positioned adjacent the container position $184_1$. The identifiers 186 and 188 are read by the instrument 102, such as by the carousel detector 154, shown in FIG. 2.

The example carousel shown in FIG. 3 has a single row of container positions arranged about a periphery of the carousel. Other embodiments include multiple rows, such as arranged along two or more concentric circles within the carousel.

Figure 4:
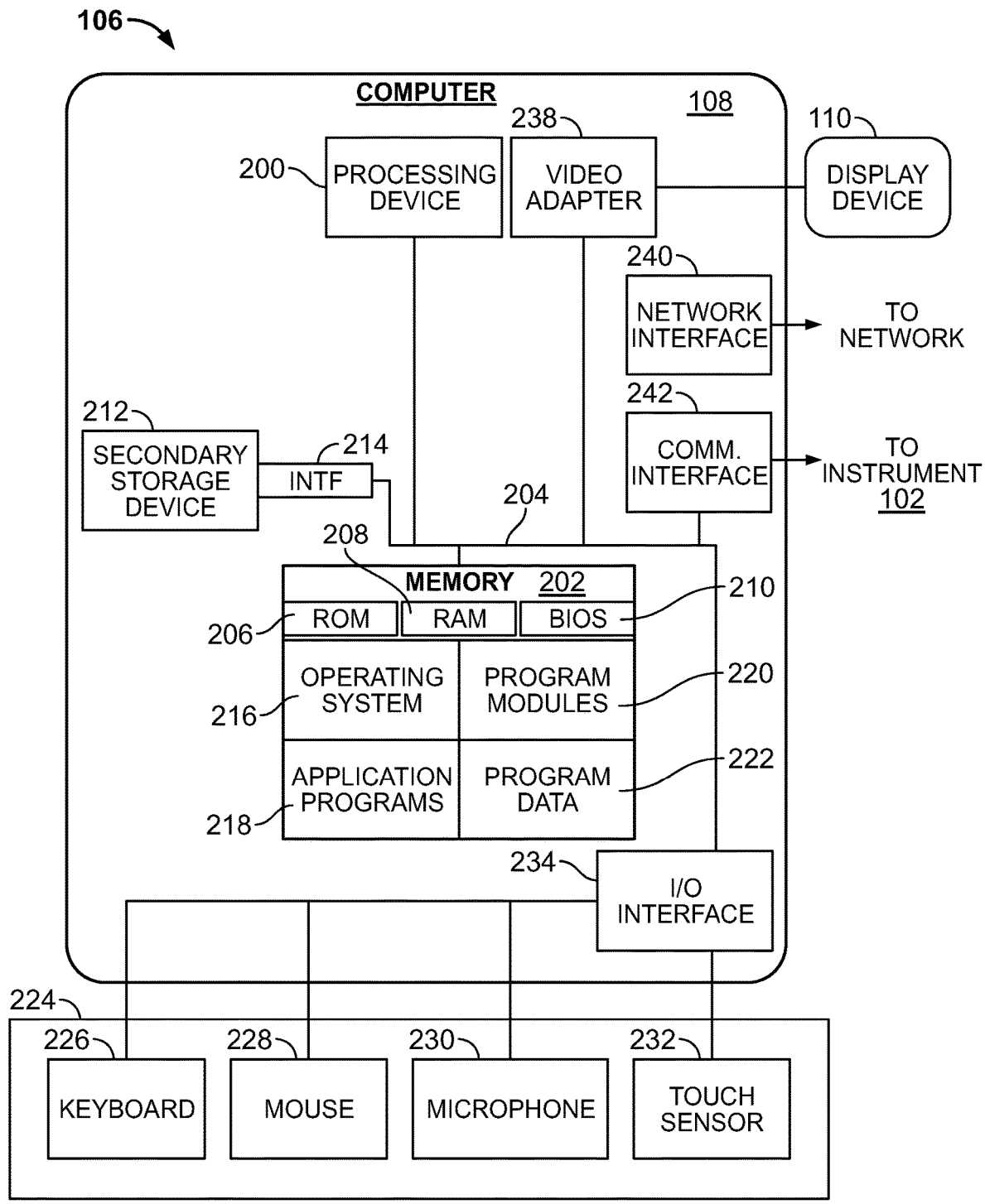
FIG. 4 is a schematic block diagram of an example of a computing device.

FIG. 4 is a schematic block diagram of an example of the computing device 106, shown in FIG. 1. FIG. 4 also illustrates an exemplary architecture of a computing device that can be used to implement various aspects of the present disclosure, including the computing device 106 or other computing devices, such as a standalone computing device used separate from the instrument 102. The computing device illustrated in FIG. 2 can be used to execute the operating system, application programs, and software modules (including the software engines) described herein, such as the instrument interface engine 112, shown in FIG. 1.

The computing device 106 includes, in some embodiments, at least one processing device 200, such as a central processing unit (CPU). A variety of processing devices are available from a variety of manufacturers, for example, Intel or Advanced Micro Devices. In this example, the computing device 106 also includes a system memory 202, and a system bus 204 that couples various system components including the system memory 202 to the processing device 200. The system bus 204 is one of any number of types of bus structures including a memory bus, or memory controller; a peripheral bus; and a local bus using any of a variety of bus architectures.

Examples of computing devices suitable for the computing device 106 include a desktop computer, a laptop computer, a tablet computer, a mobile computing device (such as a smart phone, an iPod® or iPad® mobile digital device, or other mobile devices), or other devices configured to process digital instructions.

The system memory 202 includes read only memory 206 and random access memory 208. A basic input/output system 210 containing the basic routines that act to transfer information within computing device 106, such as during startup, is typically stored in the read only memory 206.

The computing device 106 also includes a secondary storage device 212 in some embodiments, such as a hard disk drive, for storing digital data. The secondary storage device 212 is connected to the system bus 204 by a secondary storage interface 214. The secondary storage devices 212 and their associated computer readable media provide nonvolatile storage of computer readable instructions (including application programs and program modules), data structures, and other data for the computing device 106.

Although the exemplary environment described herein employs a hard disk drive as a secondary storage device, other types of computer readable storage media are used in other embodiments. Examples of these other types of computer readable storage media include magnetic cassettes, flash memory cards, digital video disks. Bernoulli cartridges, compact disc read only memories, digital versatile disk read only memories, random access memories, or read only memories. Some embodiments include non-transitory media. Additionally, such computer readable storage media can include local storage or cloud-based storage.

A number of program modules can be stored in secondary storage device 212 or memory 202, including an operating system 216, one or more application programs 218, other program modules 220 (such as the software engines described herein), and program data 222. The computing device 106 can utilize any suitable operating system, such as Microsoft Windows™, Google Chrome™, Apple OS, and any other operating system suitable for a computing device.

In some embodiments, a user provides inputs to the computing device 106 through one or more input devices 224. Examples of input devices 224 include a keyboard 226, mouse 228, microphone 230, and touch sensor 232 (such as a touchpad or touch sensitive display). Other embodiments include other input devices 224. The input devices are often connected to the processing device 200 through an input/output interface 234 that is coupled to the system bus 204. These input devices 224 can be connected by any number of input/output interfaces, such as a parallel port, serial port, game port, or a universal serial bus. Wireless communication between input devices and the interface 234 is possible as well, and includes infrared, BLUETOOTH® wireless technology, 802.11a/b/g/n, cellular, or other radio frequency communication systems in some possible embodiments.

In this example embodiment, a display device 110, such as a monitor, liquid crystal display device, projector, or touch sensitive display device, is also connected to the system bus 204 via an interface, such as a video adapter 238. In addition to the display device 110, the computing device 106 can include various other peripheral devices (not shown), such as speakers or a printer.

When used in a local area networking environment or a wide area networking environment (such as the Internet), the computing device 106 is typically connected to the network through a network interface 240, such as an Ethernet interface. Some embodiments include a wireless communication device. Other possible embodiments use other communication devices. For example, some embodiments of the computing device 106 include a modem for communicating across the network.

The computing device 106 includes a communications interface 242 that permits the computing device 106 to communicate with the instrument 102. Examples of the communications interface 242 include a universal serial bus (USB) communication device, an Ethernet communication device, a serial communication device, and a wireless communication device.

The computing device 106 typically includes at least some form of computer readable media. Computer readable media includes any available media that can be accessed by the computing device 106. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 106. Computer readable storage media does not include computer readable communication media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device illustrated in FIG. 4 is also an example of programmable electronics, which may include one or more such computing devices, and when multiple computing devices are included, such computing devices can be coupled together with a suitable data communication network so as to collectively perform the various functions, methods, or operations disclosed herein.

Figure 5:
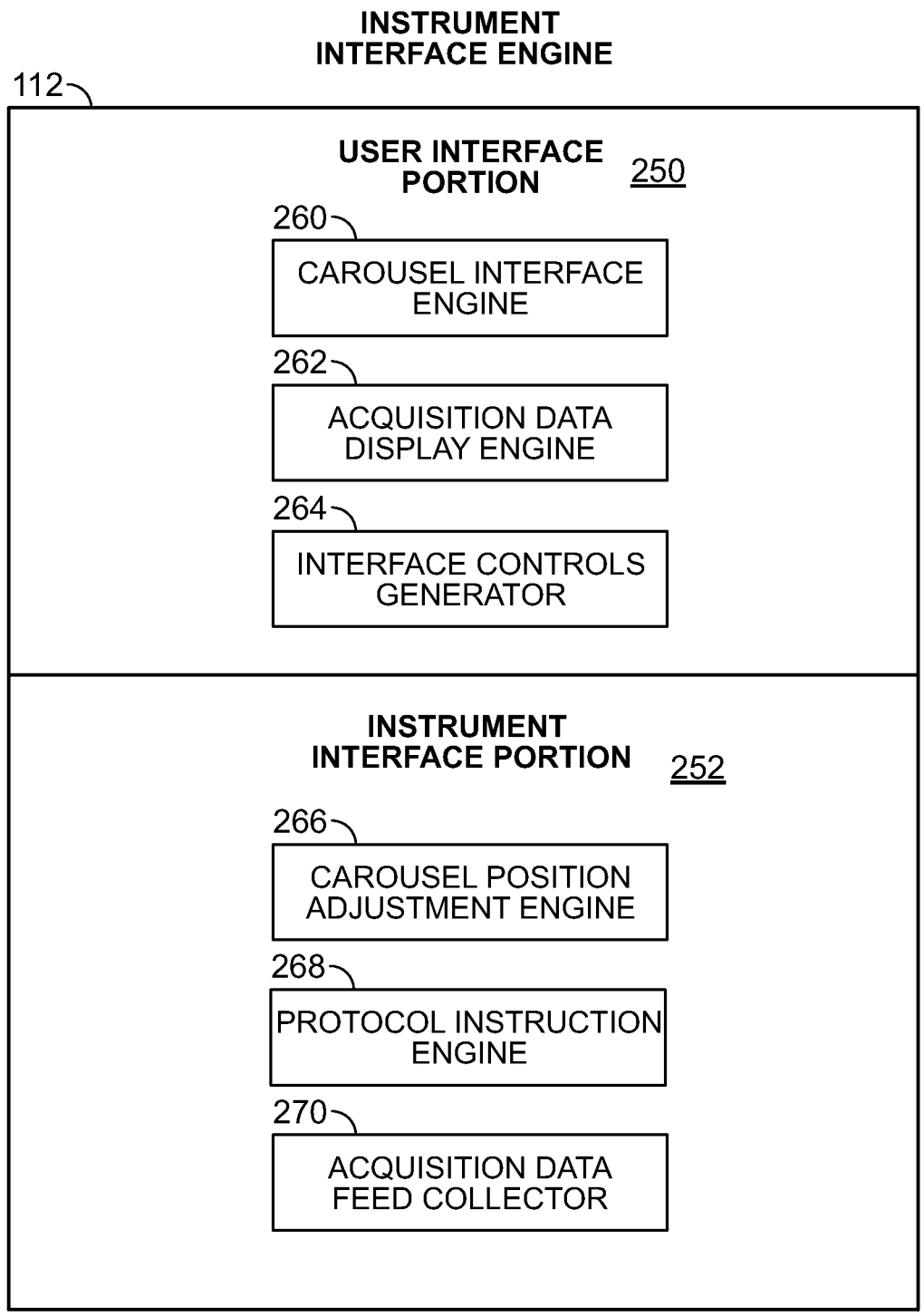
FIG. 5 is a schematic block diagram illustrating an example of an instrument interface engine executable by the computing device shown in FIG. 4.

FIG. 5 is a schematic block diagram illustrating an example of the instrument interface engine 112. In this example, the instrument interface engine 112 includes a user interface portion 250 and an instrument interface portion 252. The user interface portion 250 includes a carousel interface engine 260, an acquisition data display engine 262, and an interface controls generator 264. The instrument interface portion 252 includes a carousel position adjustment engine 266, a protocol instruction engine 268, and an acquisition data feed collector 270.

The user interface portion 250 includes components that interact with the operator, such as by generating a graphical user interface 114 (FIG. 1) and by receiving inputs through one or more input devices 224 (FIG. 4), while the instrument interface portion 252 includes components that interact with the instrument 102 (FIGS. 1-2). In one example, the instrument interface portion 252 communicates with the instrument 102 through the communications interface 242, shown in FIG. 4 to the control electronics 155 of the instrument 102, shown in FIG. 2. Although not separately illustrated in FIG. 2, the control electronics 155 typically include a communications interface compatible with the communications interface 242.

The carousel interface engine 260 operates to generate a carousel display 116, discussed in more detail herein, which includes a graphical representation of the physical carousel 104. The carousel display 116 presents information to the operator in a format that simulates the actual physical arrangement of the carousel 104 so that it is easily understood by the operator. In some embodiments the carousel display 116 also allows the user to provide inputs directly into the carousel display, such as to adjust settings or define protocols to be performed on the samples. The carousel interface engine 260 operates to generate the carousel display 116, as well as to perform the functions associated with the carousel display 116, such as described in further detail with reference to FIGS. 6-11.

The acquisition data display engine 262 operates to generate one or more graphical data displays of data obtained during the analysis of a sample. In some embodiments the acquisition data display engine 262 generates graphical plots of the acquisition data obtained by the instrument 102 while the analysis of a sample is being performed. Examples of the data displays (308) are illustrated and described in further detail with reference to FIGS. 7, 9, and 10.

The interface controls generator 264 operates to generate and display in the user interface 114 controls that are selectable by the operator to adjust the operation of the instrument 102, such as to begin the processing of samples on the carousel 104, or to stop sample analysis before the defined protocols have been completed. Examples of the interface controls are illustrated and described in more detail with reference to FIGS. 7, 9, and 10.

Turning to the instrument interface portion 252, the carousel position adjustment engine 266 operates to communicate with the instrument 102 in order to make adjustments in the position of the carousel 104 in the sample loading region 107. For example, the carousel position adjustment engine can instruct the instrument to rotate the turntable 144 (FIG. 2) so that a particular container position 184 (FIG. 3) is aligned with the sample intake system 156 (FIG. 2). Example operations of the instrument interface portion 252 are described in more detail herein, such as with reference to FIG. 9.

The protocol instruction engine 268 operates to communicate with the instrument 102 to instruct the instrument to perform a particular protocol on a sample, as defined by the operator. The protocol instructions can be provided to the instrument 102 in accordance with the instrument's defined communication protocol.

The acquisition data feed collector 270 operates to receive a data feed from the instrument 102 during the analysis of a sample. The data is then fed to the acquisition data display engine 262 where the data is plotted or otherwise displayed to the operator.

Figure 6:
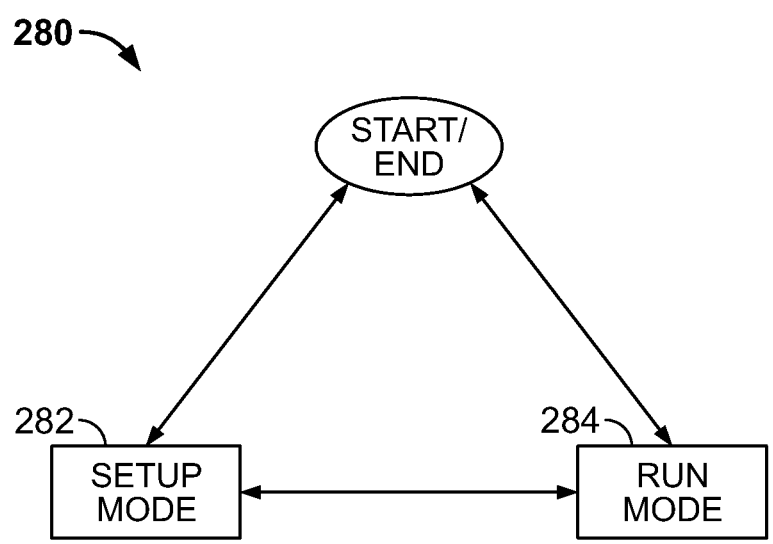
FIG. 6 is a flow chart illustrating example modes of operation of the instrument interface engine shown in FIG. 5.

FIG. 6 is a flow chart illustrating example modes 280 of operation of the instrument interface engine 112, shown in FIG. 5. In this example, the modes 280 include a setup mode 282 and a run mode 284.

Upon startup, the instrument interface engine 112 advances to the setup mode 282 or to the run mode 284.

The setup mode 282 is provided to permit the operator to configure instrument settings. As one example, the operator may interact with the instrument interface 112 to tell the instrument system 100 (FIG. 1) how to process the samples on the carousel 104. This can include, for example, identifying the locations of sample containers on the carousel, and defining protocols that the instrument 102 should follow in order to properly process and analyze the samples. In another example, the setup mode 282 permits instrument settings such as PMT voltage, PMT gains, forward scatter detection angle, and neutral density filter to be configured. An example of the instrument interface engine 112 operating in the setup mode 282 is illustrated and described in further detail with reference to FIGS. 7-9.

After the setup mode 282 is completed, the instrument interface engine 112 proceeds to the run mode 284. When in the run mode, the instrument interface engine 112 provides instructions to the instrument 102 to cause the instrument 102 to properly process and analyze the samples according to the operator's instructions provided during the setup mode 282. The instrument interface engine 112 also displays the current status of the instrument, identifies the samples that have already been processed, and which sample is currently being processed, in some embodiments. In some embodiments the run mode 284 also operates to receive and display data from the instrument 102 for presentation to the operator. An example of the instrument interface engine 112 operating in the run mode 284 is illustrated and described in further detail with reference to FIGS. 10-11.

After the run mode 284 has completed, the instrument interface engine 112 then returns to the setup mode 282 at which time the instrument can be turned off or a subsequent worklist can be configured.

In some embodiments the instrument interface engine 112 can operate on a computing device that is not part of the instrument system 100, such as because it is not communicatively connected to the instrument 102. This is useful for example to permit an operator to prepare and setup a worklist for the instrument 102 at a different location and using a separate computing device, while also preparing the carousel 104 and arranging the samples thereon. While the operator is setting up the worklist and carousel 104, the instrument system 100 remains available for use by others. After the worklist has been generated, the worklist can be saved and transferred to the computing device 106 that is part of the instrument system 100. There it can be opened and processed on the instrument system (through the run mode 284) without requiring the worklist to be defined on that computing device 106.

Figure 7:
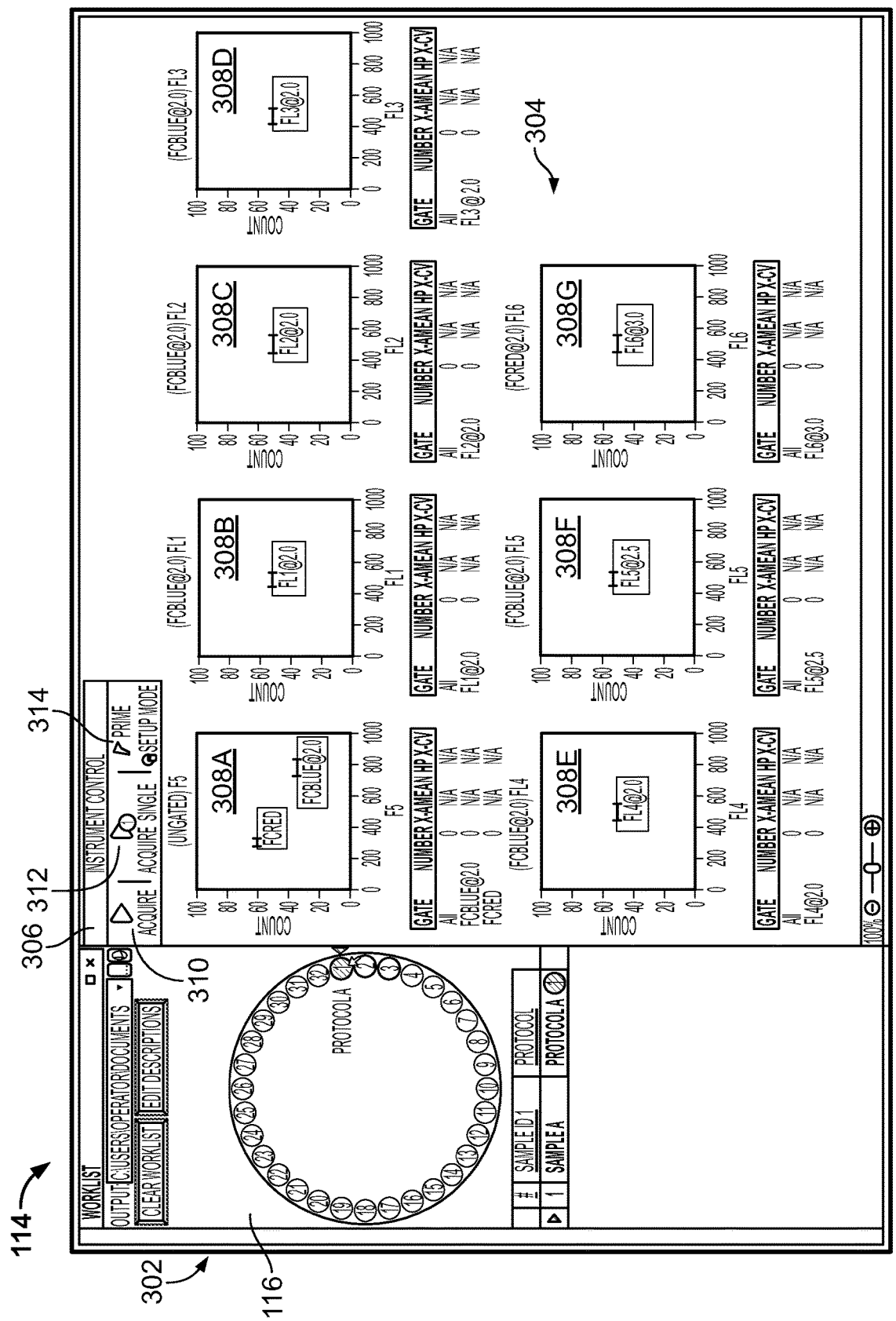
FIG. 7 is a schematic diagram illustrating an example user interface when the instrument interface engine of FIG. 4 is operating in a setup mode.

FIG. 7 is a schematic diagram illustrating an example user interface 114 generated by the instrument interface 112 when operating in the setup mode 282 (FIG. 6). In this example, the user interface 114 includes a carousel interface display region 302, an acquisition data display region 304, and an instrument controls region 306.

The carousel interface display region 302 includes the carousel display 116. In some embodiments the carousel display 116 is generated by the carousel interface engine 260, shown in FIG. 5.

The carousel display 116 includes a graphical representation of the carousel 104. In some embodiments the carousel display 116 operates to graphically display to the operator the instructions that have been defined for processing the samples on the carousel 104, and also to receive inputs from the operator therein to define or change those instructions.

In some embodiments the carousel interface display region 302 receives inputs from the operator to generate a worklist including one or more protocols for processing of the samples on the carousel 104. Once completed, the worklist data is communicated to the instrument 102, and the instrument 102 uses the data to acquire samples from the appropriate carousel locations and process and analyze the samples according to the defined protocols. An example of the carousel interface display region 302 is illustrated and described in further detail with reference to FIGS. 8-11.

The acquisition data display region 304 is a portion of the user interface 114 in which data from the instrument 102 is displayed when operating in the run mode 284 (FIG. 6). When operating in the setup mode 282, as shown in FIG. 7, the acquisition data display region 304 can be configured by the operator to select and arrange the desired one or more data displays that the operator wants included in the acquisition data display region 304 during the analysis of the sample selected in the carousel interface display region 302.

A variety of data displays 308 (e.g., 308A-G) are available for inclusion in the acquisition data display region 304, in some embodiments, such as including histograms, dot plots, and density plots. A histogram provides a graphical representation as a frequency distribution, where the height depicts corresponding frequencies. A dot plot compares two parameters to graphically represent their relationship. Each event that contains markers for the two sets of data being compared appears as a dot in the dot plot. A density plot is a multi-color representation of the number or percentage of events that occur in comparing X-axis and Y-axis parameters. Greater and lesser density of event occurrences are represented by different colors. In some embodiments the data displays 308 are selectable from a menu of available options, or by dragging and dropping the data displays 308 from the menu into the desired location within the acquisition data display region 304. The data displays 308 are adjustable by the operator, such as to enlarge or shrink the data displays 308, or to rearrange or reposition the data displays within the acquisition data display region 304. In some embodiments gates or other tools are provided to allow further customization of the displays 308. Examples of gates and tools include: linear, quadrant, hinged, polygon, freehand, rectangle, and ellipse.

The instrument controls region 306 generates and displays instrument controls that are selectable by the operator to control the instrument 102. For example, in some embodiments the instrument controls region 306 includes acquire control 310, acquire single control 312, and prime control 314. The acquire control 310 initiates the processing and analysis of the samples according to the worklist defined in the carousel interface display region 302. In contrast, selection of the acquire single control 312 initiates the processing and analysis of only a single sample that is selected in the carousel interface display region 302. Selection of the prime control 314 initiates the performance of a priming operation by the instrument 102.

Figure 8:
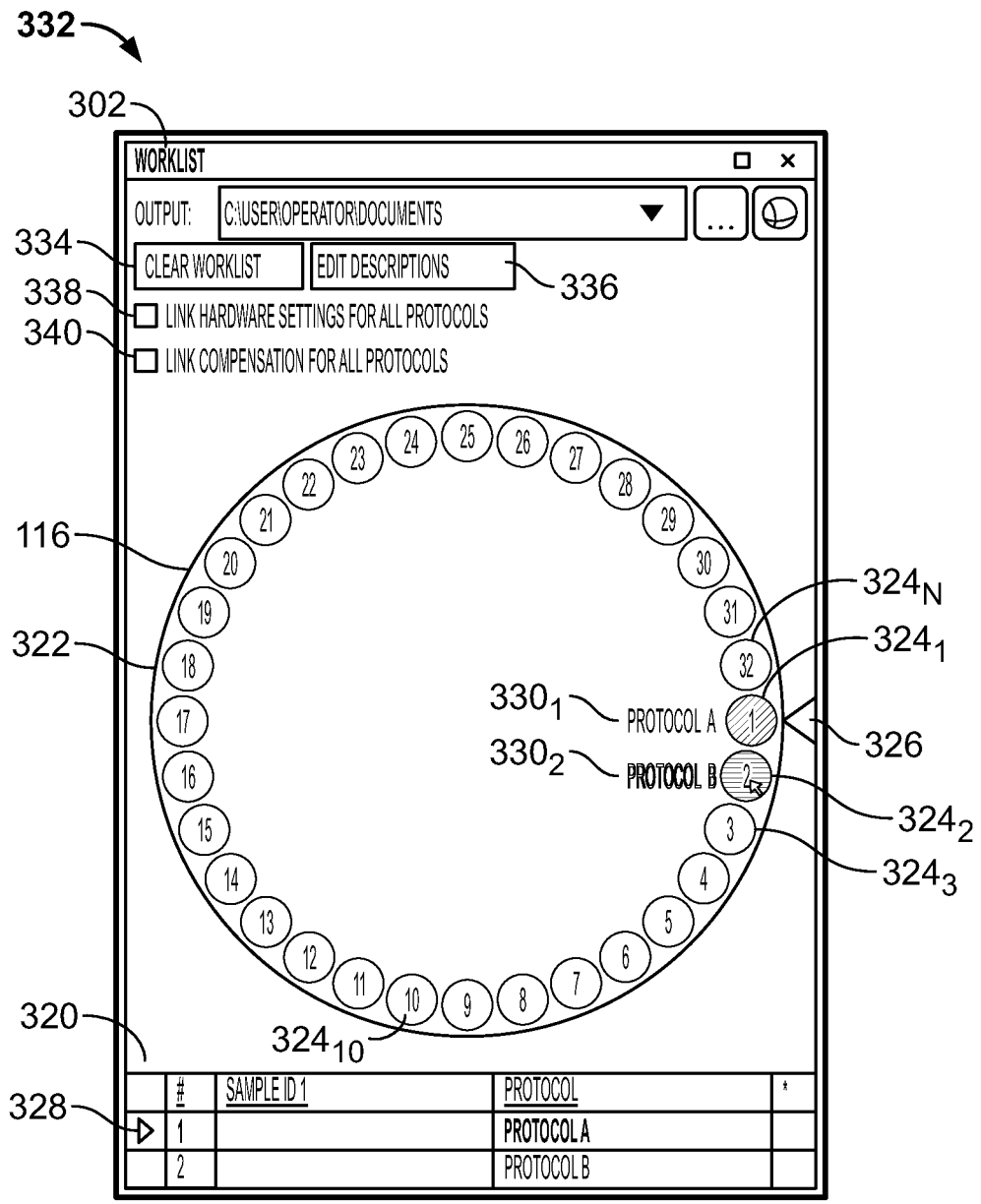
FIG. 8 is a schematic diagram illustrating an example of a carousel interface display region of the user interface shown in FIG. 7.

FIG. 8 is a schematic diagram illustrating an example of the carousel interface display region 302, shown in FIG. 7. In this example, the carousel interface display region 302 includes the carousel display 116 and a data specifications grid 320.

Figure 11:
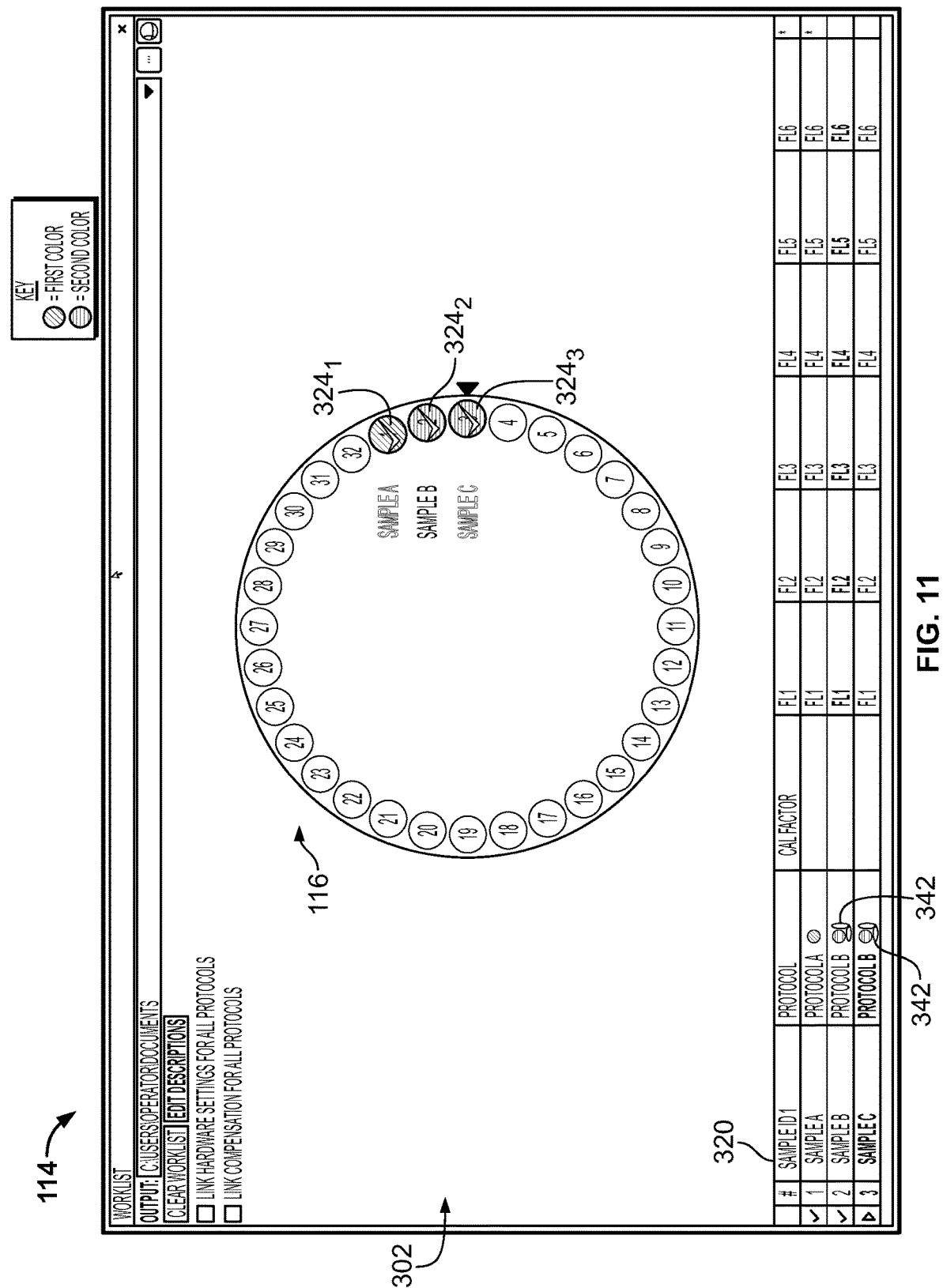
FIG. 11 is a schematic diagram illustrating an example user interface including the carousel interface display region operating in an expanded display mode.

The carousel interface display region 302 operates to receive inputs from the operator to allow the operator to provide details about the samples loaded onto the carousel 104. For example, in some embodiments the operator can utilize the carousel interface display region 302 to do one or more of the following: identify which of the carousel positions contain a sample, give each sample a name, assign a protocol to each sample, link protocols, and make parameter specifications. The carousel interface display region 302 can be viewed as a portion of the user interface as shown in FIG. 7, or can be displayed on its own in an expanded view such as shown in FIGS. 8 and 11.

In this example, the carousel display 116 includes a graphical representation of the physical carousel 104. In this example the graphical representation is presented as a top view of the carousel 104, and other views can also or alternatively be used, such as isometric or side views. The example carousel display 116 includes the body 322 and container positions 324. The body 322 is a graphical representation of the body 180 (FIG. 3) of the carousel, such as having a circular shape. Distributed about the perimeter of the body 322 are container positions 324 (including container positions $324_1$, $324_2$, . . . $324_N$), which graphically represent the locations of the container positions 184 (FIG. 3) of the carousel 104. In this example, the carousel 104 includes 32 container positions 184, and therefore the carousel display 116 also includes 32 container positions. Other embodiments include other quantities of container positions to match the quantity of container positions in the carousel 104. In this example the container positions 324 are each represented by a circular shape. Further, in this example, each container position 324 contains a number within the circular shape identifying the order of each position 324 on the carousel, such as starting with a position 1 and continuing consecutively to position 32. The container positions 324 can contain different colors, as discussed in further detail herein.

The data specifications grid 320 is provided in some embodiments to display and receive additional data specifications for the samples contained in the carousel 104 and the protocols to be performed on the samples by the instrument 102. In this example, the data specifications grid 320 includes a plurality of rows and columns. Each row in the grid represents a sample at a given container position 324, and the columns contain data related to that sample. In this example, the columns identify a currently selected sample, a container position, a sample identification, and a protocol for each sample. More, fewer, or different columns are included in other embodiments. For example, in some embodiments an expanded view is also available in which additional columns are displayed. Several examples of possible additional columns (not shown in FIG. 8) include one or more additional sample identification columns, a calibration factor column, and one or more detector description columns (to permit the operator to provide descriptions of the detectors to be used by the instrument 102).

Figure 9:
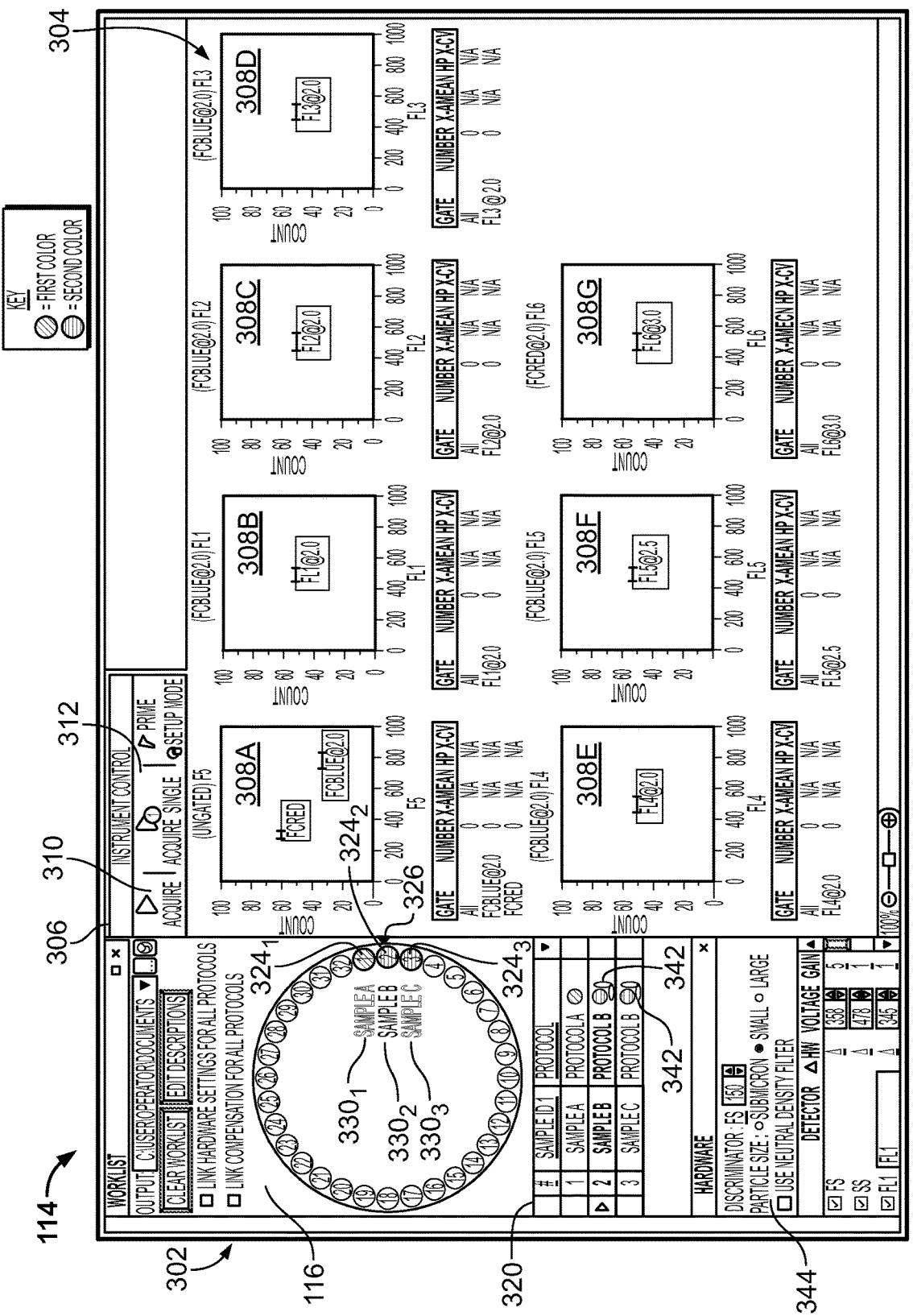
FIG. 9 is another schematic diagram of the example user interface shown in FIG. 7, operating in the setup mode and including a completed worklist.

In some embodiments, the data specifications grid 320 displays link icons 342 (such as visible in FIG. 9). When a container position 324 is selected in the carousel display 116, the instrument interface engine 112 (FIG. 5) determines whether the selected container position 324 is linked (as discussed in further detail herein) with any other container positions. If so, link icons are displayed in the row associated with the selected container position 324, as well as in the rows associated with the container positions that are linked to the selected container position 324. One example of a link icon is a graphical representation of two links of a chain, suggesting that the selected container position is linked with another container position. In some embodiments the link icon further includes a color indicator, such as a filled circle. The filled circle has a color matching the color of the container position shown in the carousel display 116, and represents the protocol that has been defined for the selected container position.

When operating in the setup mode, the operator may interact with the carousel display 116 and the data specifications grid 320 to provide information about the samples loaded onto the carousel or to define protocols to be performed on the samples by the instruments. In some embodiments, this functionality is also available during the run mode and/or other modes of operation.

In some embodiments, the carousel display 116 interacts with the operator to generate a worklist. The worklist is a set of instructions that define the order and operations that should be performed by the instrument. In some embodiments the worklist includes one or more of: an identification of the quantity of sample containers on the carousel 104, an identification of the positions of the sample containers, an indication and/or definition of a protocol to perform on the samples contained in the sample containers, meta information (such as a sample identification number or a description), an order in which the samples should be processed.

In one example, the container positions 324 are selectable by providing an input onto the container position 324. For example, the operator manipulates an input device to select a point on the container position $324_2$ using a suitable input (such as a click, double click, tap, double tap, or other input). The instrument interface engine 112 recognizes the input and selects the corresponding container position $324_2$. Once selected, in some embodiments, the carousel display 116 animates rotation of the carousel until the selected container position $324_2$ is positioned at the origin position 326. In addition, the indicator 328 is moved from its previous position to the row associated with the selected container position $324_2$ (#2) in the data specifications grid 320, in some embodiments.

To indicate that a sample is present at a particular location on the carousel, the operator selects the appropriate container position and identifies a protocol to be run on the sample at that position. As one example, the operator provides an input into the container position 324, such as a right click or other input, and a pop-up menu is displayed (not shown in FIG. 8). From the menu the operator can choose to create a new protocol or import a previously defined protocol. If a new protocol is created, or an existing protocol is modified, the operator can also choose to save the protocol for future use from this same menu.

In some embodiments a protocol includes data identifying one or more, or all of the following: which hardware detectors are enabled, which measurement(s) to collect from each detector, collection angle for forward scatter, status of neutral density filter for side scatter, specification of discriminator parameter, specification of discriminator value, voltage and gain for each detector, label for each detector, set of plots to display and all associated configuration information, stop conditions specification, flow rate specification, compensation values, gates and associated parameters (color, precedence, names, for example), and protocol name.

Samples can be arranged anywhere on the carousel 104, and accordingly, in some embodiments the operator is allowed to indicate the presence of a sample container anywhere on the carousel display 116. In the example shown in FIG. 8, if the carousel 104 contains a sample container at container position 10, the operator can simply select the container position $324_{10}$ in the carousel display 116 and define a new protocol or import a previously defined and saved protocol for that container position $324_{10}$. In some embodiments, after the protocol has been defined, the carousel display 116 rotates so that container position $324_{10}$ is aligned with the origin 326. In some embodiments, if another container position 324 (e.g., container position $324_1$) already includes the desired protocol, the operator can alternatively copy the protocol from the container position $324_1$ to the container position $324_{10}$, such as by providing a drag and drop input while depressing the CTRL key or other function key, or in another embodiment, by selecting the position $324_1$ having the desired protocol (such as with a right-click operation) and selecting a "duplicate" option from the pop-up menu. The protocol is then reproduced in the next available position (e.g., $324_2$), which can then be dragged and dropped to the desired position.

Once a protocol has been defined for the sample at the selected container position 324, the color of the container position 324 is changed from an initial color to a different color indicating that a sample is expected to be present at that container position 324 during the acquisition, and that the protocol has been defined for the sample. This color coding allows the operator to visually identify the container positions for which a protocol has been defined, and also to visually identify those container positions for which a protocol has not been defined, without having to individually check the settings of each container position 324 to determine whether or not a protocol has been defined.

If the operator wants to perform the same protocol on a number of samples, the carousel display 116 can be used to easily replicate the protocol among other container positions 324. In one example, a container position 324 having the desired protocol previously defined is selected and an input is provided indicating a desire to duplicate the protocol to another container position 324. An example of the input is a duplicate command, which may be performed by selecting "duplicate" from a menu, or by providing a drag and drop input while depressing a function key (such as the CTRL key), for example. Another example of the input is a right click input followed by selection of a duplicate option from the pop-up menu, in which case the protocol may be duplicated to the next available container position 324 on the carousel. This allows protocols to be quickly and easily replicated to additional container positions so that the operator does not have to redefine the same protocol for each container position for which that protocol will be assigned. Similarly, if the operator wants to define a protocol that is very similar to a previously defined protocol, the protocol can be replicated to another container position in this way, and then edited to make the desired modifications for that container position. Accordingly, in some embodiments replication of protocols allows protocols to be defined more quickly, with less user input, in less time, and reduces the chance that errors occur in the process.

Groups of protocols can also be moved or copied simultaneously in some embodiments of the carousel display 116. For example, if the operator wanted to have a repeating pattern of Protocol A and Protocol B, the operator could select those protocols at the container positions $324_1$ and $324_2$, and then copy them to the next positions $324_3$ and $324_4$, and then to the next positions, and so on, until the desired pattern is defined. To select the group the operator provides a group selection input. An example of a group selection input is clicking on the respective container positions 324 while holding down a key, such as the SHIFT key, or by using a pointer input to draw a selection box around the group of container positions 324. The copy operation can therefore be used to copy a group of protocols from one set of container positions to another set of container positions. The group of protocols can include a single protocol or multiple different protocols, such as in a repeating pattern. Accordingly, in some embodiments the copy operation allows protocols to be defined more quickly, with less user input, in less time, and reduces the chance that errors occur in the process.

Some embodiments include a linking function. The linking function permits a set of two or more container positions 324 to be linked together. When linked together, changes made to a protocol for one of the linked container positions 324 is automatically adjusted for all other linked container positions 324. For example, if five container positions 324 are linked together, the operator can make a change in the protocol for one of the container positions, and that change is automatically made to the protocol of the other four container positions, so that the operator does not have to separately make the changes for all five container positions. In some embodiments linked container positions are graphically identified by a link icon 342 discussed with reference to FIG. 9, and/or by a common color coding, for example. In addition to saving time and reducing the number of user inputs required, the linking function also reduces the chance of error by visually indicating those protocols that are linked together. This allows the user to quickly verify that a set of container positions are properly linked together, and thereby ensure that they all share the same protocol. It also reduces the chance of error by not requiring the user to separately input and modify protocols for each container position that shares the common protocol.

In some embodiments, linked container positions 324 are represented by a common color, and accordingly container positions 324 that are not linked are represented by different colors. Linked protocols can be unlinked, for example, by providing an input such as a right-click, and selecting "unlink" from the pop-up menu. Once a previously linked protocol is unlinked, the color of the container position 324 is changed to a different color indicating that the container position 324 is no longer linked to the other one or more container positions 324. The color coding provides the user with a quick and easy way to visually verify that container positions 324 that are supposed to have a common protocol have the same color, and container positions 324 that are supposed to have different protocols do not have the same color, for example.

In some embodiments an operator can also provide meta information that is associated with a container position 324. In the example shown in FIG. 8, the container positions $324_1$ and $324_2$ include labels 330. In some embodiments, or in the absence of other meta information, the labels 330 display the names of the protocols, such as Protocol A and Protocol B, respectively. In some embodiments, meta information can also or alternatively be displayed at this location in the carousel display 116. For example, the operator can select the labels 330 and enter meta information, such as a sample identifier, a description, or any other desired information. The meta information is then displayed in the respective label. As another option, the operator can select the appropriate field in the sample ID column of the data specifications grid 320 and input the meta information into that (or another) field. Once entered, the meta information is displayed in the label 330 in some embodiments. The meta information can be helpful to display various information, such as a name of a protocol, a type of a protocol, a source of a sample, a type of a sample, or a variety of other information. As a result, the meta information can be helpful to the operator in properly setting up the protocols, and in verifying that the protocols have been properly setup, such as by comparing the meta information with the color coding. For example, if the meta information shows a repeating pattern of "protocol A" and "protocol B," the color coding of the container positions 324 can be compared with the pattern shown in the meta information to verify that the color coding has the same pattern.

Some embodiments of the carousel interface display region 302 include additional features. For examples, some embodiments include an output file selection region 332 which identifies a directory where the acquired data files will be stored containing the data for the acquisition. The output file selection region 332 can be used to select an alternate directory for the storage of the acquired data files. As another example, the user interface 114 can also include a clear worklist control 334 and an edit descriptions control 336. In this example, the clear worklist control 334 clears the data from all container positions and the carousel display 116 is updated to show a graphical representation of an empty carousel. The data specifications grid 320 is also cleared. The edit descriptions control 336 is selectable in some embodiments to open an expanded view that shows additional columns in the grid display, where the operator can edit the labels of the detectors as well as provide additional metadata. In another possible embodiment, the edit descriptions control 336 is selectable to convert the labels 330 into text entry fields so that the operator can change or add meta information directly into the carousel display 116 to be displayed by the labels 330. Some embodiments include controls 338 and 340. The control 338 can be selected to link settings between all protocols. Examples of such settings include the voltage, gains, and discriminator settings. Once linked, changes made to the settings of one protocol affect the settings for all other protocols as well. The control 340 can be selected to link the compensation values between all protocols. Once linked, changes made to the compensation in one protocol affect the compensation of all other protocols as well.

FIG. 9 is another schematic diagram of the example user interface 114 shown in FIG. 7, operating in the setup mode and including a completed worklist. As in FIG. 7, the example instrument interface 112 includes the carousel interface display region 302, the acquisition data display region 304, and the instrument controls region 306.

This example illustrates the instrument interface 112 after the generation of a worklist in the carousel interface display region 302. The worklist is displayed in both the carousel display 116 and in the data specifications grid 320, which show that samples will be provided on the carousel 104 at container positions $324_1$, $324_2$, and $324_3$. Additionally, protocols have been selected for each of the three container positions 324. A first protocol ("protocol A") is assigned to container position $324_1$, and a second protocol ("protocol B") is assigned to container positions $324_2$ and $324_3$. Additionally, sample ID's containing meta information are displayed in labels 330, showing that container position $324_1$ contains "sample A" (label $330_1$) container position $324_2$ contains "sample B" (label $330_2$), and container position $324_3$ contains sample C" (label $330_3$). Further, the container position $324_1$ is shown with a first color associated with the first protocol, and container positions $324_2$ and $324_3$ are shown in a second color associated with the second protocol. The common color of container positions $324_2$ and $324_3$ shows that they are assigned to the same protocol, and also that they are linked together. The link is also shown by the presence of the link icons 342 in the data specifications grid 320.

This example also illustrates an example hardware interface region 344. The hardware region is one example of an interface that the operator can use to define or modify a protocol for a container position 324. In this example, the protocol includes hardware configuration options, such as including a discriminator option, a particle size option, an option to include a neutral density filter, and options to select from various available detectors and detector settings. In some embodiments multiple detectors are available, including detectors operable to detect light of different wavelengths (e.g., 488 nm, 638 nm, and 405 nm). Examples of detector setting include whether a particular detector is active, a detection mode (e.g., area, height, or width ("AHW")), a voltage, and a gain.

After the worklist has been completed, the operator then utilizes the controls in the instrument controls region 306 to initiate the run mode 284 (FIG. 6) to begin the acquisition of data and analysis of the one or more samples. As one example, the operator selects control 310 to initiate the run mode 284 and acquisition based on the worklist.

If the operator wants to process only one sample, the operator can instead use the acquire single control 312. For example, the operator selects the container position $324_1$ to be processed. The carousel display 116 then rotates so that the container position $324_1$ is arranged at the origin 326. The operator then selects the acquire single control 312 to initiate the run mode 284 (FIG. 6) and processing of the single sample according to the protocol (protocol A) assigned to the selected container position $324_1$.

Upon initiation of the run mode 284, the instrument interface engine 112 (FIG. 5) communicates with the instrument 102 to perform the acquisition defined in the carousel interface display region 302. For example, the carousel position adjustment engine 266 instructs the control electronics 155 to rotate the carousel 104 to the starting position, in which the first container position 184 (e.g., $184_1$, FIG. 3) is arranged so that the sample container 190 is accessible by the sample intake system 156. The protocol instruction engine 268 provides instructions to the instrument 102 defining the protocol to be performed on the sample, and initiating the analysis of the sample according to the protocol. As data is generated by the instrument 102, it is communicated to the acquisition data feed collector 270. The data is used by the acquisition data display engine 262 to generate one or more data displays in the acquisition data display region 304.

Figure 10:
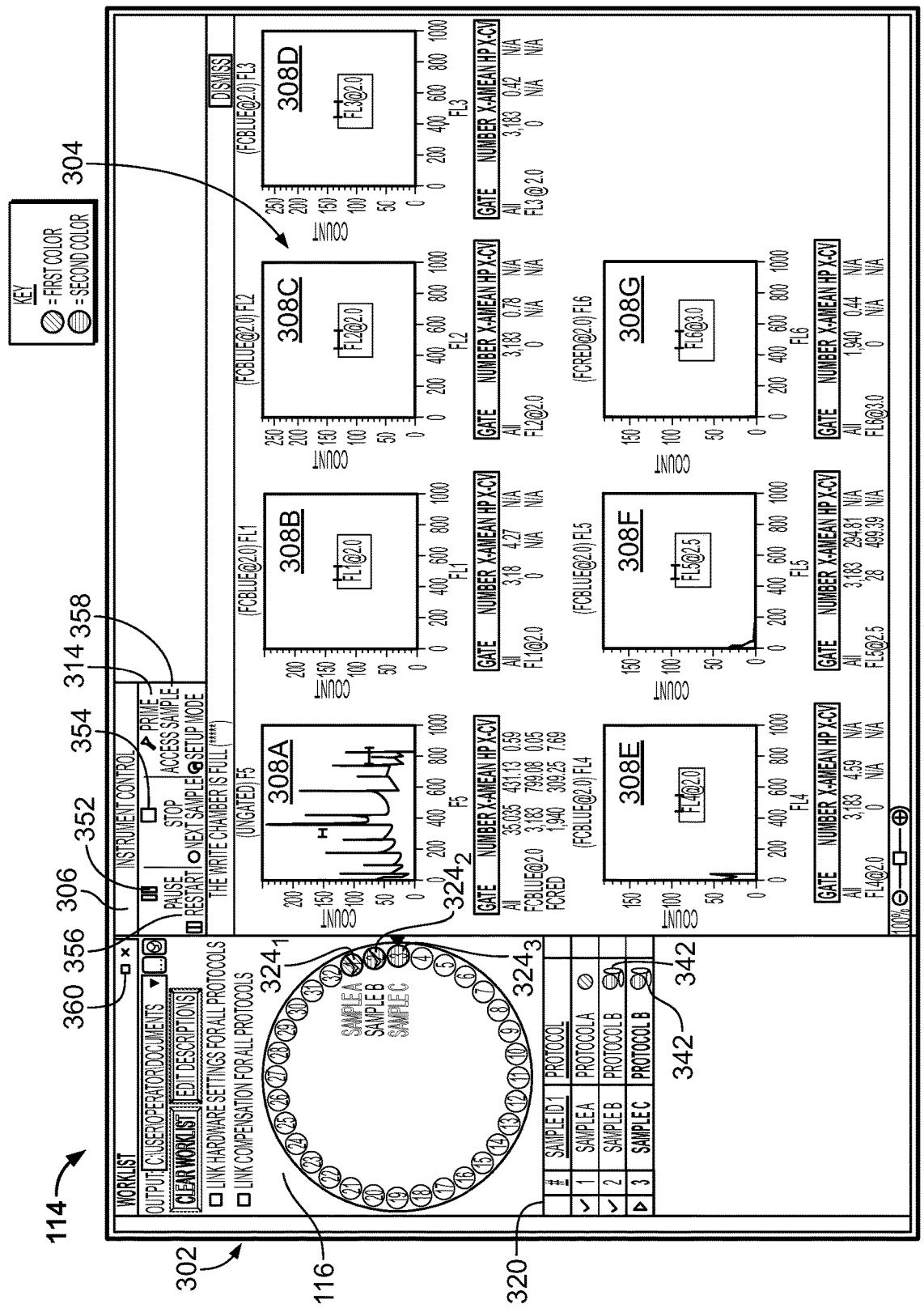
FIG. 10 is a schematic diagram illustrating an example of the user interface, shown in FIG. 7, operating in a run mode.

FIGS. 10-11 illustrate an example of the user interface 114 while operating in the run mode 284, shown in FIG. 6.

FIG. 10 is a schematic diagram illustrating an example of the instrument interface 112, while the instrument interface 112 is operating in the run mode 284 (FIG. 6). The instrument interface 112 includes the carousel interface display region 302, the acquisition data display region 304, and the instrument controls region 306.

When operating in the run mode 284, the carousel interface display region 302 operates to display a current status of the acquisition, while the instrument interface engine 112 operates to control the instrument 102 to perform the acquisition according to the instructions defined in the worklist.

For example, in some embodiments the carousel display 116 shows the current position of the carousel 104 in the sample loading region 107. In the example shown in FIG. 10, the carousel display 116 shows the container position $324_3$ positioned at the origin 326, indicating that the sample container at the container position $184_3$ (FIG. 3) is currently at the origin where it can be accessed by the sample intake system 156 (FIG. 2). When the instrument 102 rotates the carousel 104, the carousel display 116 also rotates to show the current arrangement of the carousel 104 in the sample loading region 107.

In some embodiments the container positions 324 operate as progress indicators. For example, as the sample from the container position $184_3$ is being processed, the instrument interface engine 112 generates an estimate of a progress percentage (e.g., the percent of the processing that has been completed for the current sample), and generates a progress indicator at the container position $184_3$ graphically depicting the progress percentage. As one example, the graphical depiction includes a horizontal line extending across the container position 324, where the height of the line corresponds to the progress percentage, such that the line is at the top of the container position 324 at the start of processing (0% completed), half way down when the processing is about 50% completed, and at the bottom at the end of processing (100% completed). In some embodiments a space between the line and the top or the bottom of the container position 324 is filled with a different color than the rest of the container position 324. In some embodiments the progress indicator has the appearance of a liquid that is being drained from or filled into the container position, for example. The progress indicator can alternatively be rotated and advance in any other orientation as desired in other embodiments, such as upside down or sideways, to convey the same information. Other examples of progress indicators include a speedometer-type display, a clock-type display, a spot that expands to fill a circle, a rotating graphic that forms a circle when complete, or a variety of other possible progress indicators.

After the processing of a sample has been completed, the container position 324 is updated to include a completion icon, in some embodiments. An example of a completion icon is a check mark, such as shown in the container positions $324_1$ and $324_2$. Additionally, some embodiments include a status column within the data specifications grid 320 that shows the status of the worklist processing. In this example, the status column includes completion icons, such as check marks, after a sample has been processed, is blank when a sample is awaiting processing, and includes a current sample indicator, such as an arrow or right-pointing triangle, to identify the sample currently being analyzed by the instrument 102.

As a sample is being analyzed, the data acquired for that sample is displayed in one or more data displays 308 within the acquisition data display region 304.

When operating in the run mode 284, the instrument controls region 306 changes to remove the acquisition controls 310 and 312, and to include a pause control 352, a stop control 354, a restart control 356, and an access sample control 358. The pause and stop controls 352 and 354 are selectable to cause the instrument interface engine 112 (FIG. 5) to pause or stop the acquisition, respectively. The restart control 356 is selectable to cause the instrument interface engine 112 to restart the processing of the currently acquiring sample. The access sample control 358 is selectable to cause the instrument interface engine 112 to pause the acquisition and unlock the cover 146 (FIG. 2) of the sample loading region 107 so that the operator can access the carousel 104, sample containers 190, and samples contained therein.

Some embodiments include an expand control 360 associated with the carousel interface display region 302. Selection of the expand control 360 causes the user interface 114 to convert to an expanded display mode as shown in FIG. 11.

FIG. 11 is a schematic diagram illustrating an example user interface 114 including the carousel interface display region 302 operating in an expanded display mode. In this example the carousel interface display region 302 includes the carousel display 116 and the data specifications grid 320.

The expanded display mode expands the carousel display 116 so that it takes up at least a majority of the window or viewable surface of the display device 110 (in at least one dimension). The expanded view allows the operator to more easily view the carousel display 116, such as to easily see the status of the acquisition as it progresses. Further, it may permit the operator to move farther away from the computing device 106, while allowing the operator to continue monitoring the status of the acquisition from that farther location.

In some embodiments the expanded display includes a carousel display 116 that is larger in size than the carousel display 116 when in the unexpanded configuration, such as shown in FIG. 10.

Figure 12:
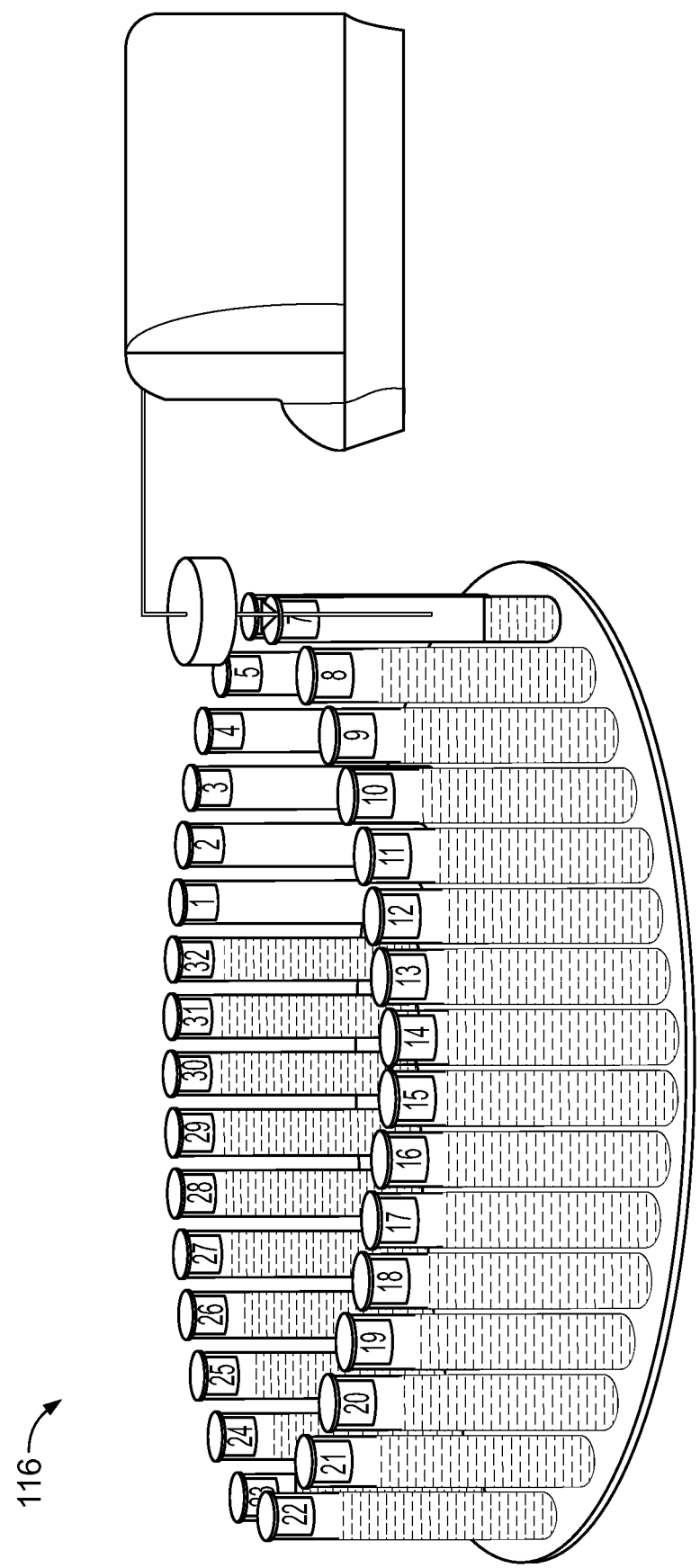
FIG. 12 is a schematic diagram illustrating another example of a carousel interface display region.

FIG. 12 is a schematic diagram illustrating another example of the carousel display 116. In this example, the carousel display 116 includes a graphical representation of the carousel 104 (FIG. 3), as well as graphical representations of sample containers and the samples contained therein. In this example, the carousel display 116 includes an isometric graphical representation of a carousel. At least some embodiments include a three-dimensional graphical representation of a carousel, such as shown in FIG. 12.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. An instrument system comprising:
an instrument configured to analyze samples;
a carousel comprising a body and a plurality of container positions arranged around an outer perimeter of the body, the plurality of container positions configured to support a plurality of sample containers containing the samples to be analyzed by the instrument; and
a computing device including a display, the computing device configured to generate a user interface displaying a top view carousel display that depicts the plurality of container positions, wherein the top view carousel display is configured to receive inputs from an operator directly into the depiction of the plurality of container positions to define instructions for analysis of the samples by the instrument.

2. The instrument system of claim 1, further comprising a pointer input device, wherein at least some of the inputs are received from the operator through the pointer input device.

3. The instrument system of claim 1, wherein the top view carousel display further includes depictions of:
the body; and
at least one sample container arranged in at least one of the plurality of container positions.

4. The instrument system of claim 3, wherein the depiction of the sample container is color coded with a color representing a protocol defined for the sample container.

5. The instrument system of claim 4, the depictions including a plurality of sample containers, wherein sample containers assigned a common protocol have a common color, and wherein sample containers assigned different protocols have different colors.

6. The instrument system of claim 3, the depictions further including labels adjacent to at least some of the container positions, the labels displaying text-based information associated with the adjacent container positions.

7. The instrument system of claim 1, the depiction of the sample container including a completion icon indicating that a sample associated with the sample container has been analyzed by the instrument.

8. The instrument system of claim 1, wherein sample containers having a common color are linked, such that an adjustment to a protocol of one of the linked sample containers results in an adjustment to the protocol of the other linked sample containers.

9. The instrument system of claim 1, wherein at least one of the instructions causes the instrument to rotate the carousel based on the instruction.

10. The instrument system of claim 1, wherein the user interface further displays a data specifications grid including a plurality of rows and columns, wherein at least some of the columns are associated with the plurality of container positions of the carousel.

11. The instrument system of claim 1, wherein the instrument is a flow cytometer.

12. The instrument system of claim 1, the top view carousel display further including a depiction of a presentation unit body.

13. The instrument system of claim 12, wherein the inputs include a selection input received directly into the depiction of the plurality of container positions.

14. The instrument system of claim 12, wherein the inputs include a drag and drop input from a first container position to a second container position, wherein upon receipt of the drag and drop input, a protocol associated with the first container position is transferred to the second container position.

15. The instrument system of claim 1, wherein the top view carousel display is further configured to receive inputs from the operator to provide details about the samples loaded onto the carousel.

16. The instrument system of claim 1, wherein the top view carousel display depicts a first container position for a first container, wherein the top view carousel display is configured to receive an input from the operator selecting the depiction of the first container position and receive an input from the operator defining a set of instructions of the first container.

17. The instrument system of claim 16, wherein the top view carousel display depicts a second container position for a second container, wherein the top view carousel display is configured to receive an input from the operator defining a set of instructions for the first container by copying a set of instructions previously defined for the second container.

18. The instrument system of claim 1, wherein the top view carousel display is further configured to receive inputs from the operator to provide meta information associated with a container position.

19. A computing device comprising:
a display device;
at least one processing device; and
at least one computer readable storage device, the computer readable storage device storing data instructions, which when executed by the at least one processing device cause the at least one processing device to:
generate a user interface on the display device, the user interface displaying a top view carousel display that depicts a plurality of container positions arranged around an outer perimeter of a body of a carousel, wherein the plurality of container positions of the carousel are configured to support a plurality of sample containers containing samples to be analyzed by an instrument; and
receive inputs, at least one of the inputs being received directly into the depiction of the plurality of container positions, the inputs defining instructions for analysis of a sample by the instrument.

20. The computing device of claim 19, wherein the at least one input is a selection input received directly into the depiction of the plurality of container positions.

21. The computing device of claim 20, wherein the selection input is a tap input received by a touch sensitive display device of the computing device.

22. The computing device of claim 20, wherein the selection input is received through a pointer input device selected from a mouse, a touch pad, or a track ball, by moving a pointer into the depiction of the plurality of container positions and providing a selection input selected from a click, a tap, or a press.

23. The computing device of claim 19, wherein the at least one input is a drag and drop input from a first container position to a second container position, wherein upon receipt of the drag and drop input, a protocol associated with the first container position is transferred to the second container position.

24. A method of operating an instrument, the method comprising:
processing one or more samples with the instrument, the one or more samples being contained in sample containers supported in a plurality of container positions arranged around an outer perimeter of a body of a carousel; and
generating a user interface with a computing device during the processing of the one or more samples, the user interface displaying a top view carousel display that depicts the plurality of container positions, wherein the top view carousel display shows a current status of the processing of the one or more samples and is configured to receive inputs from an operator directly into the depiction of the plurality of container positions to define instructions for the processing of the one or more samples by the instrument.

25. The method of claim 24, wherein the top view carousel display extends across at least a majority of a viewable surface of a display device in at least one dimension.

26. The method of claim 24, wherein the top view carousel display includes a completion icon for each sample container that has been processed by the instrument to show the current status of the processing of the one or more samples.

* * * * *